US00PP21357P3

(12) United States Plant Patent
Kobelt

(10) Patent No.: US PP21,357 P3
(45) Date of Patent: Oct. 5, 2010

(54) **VARIETY OF *RUBUS* PLANT NAMED 'SUGANA'**

(50) Latin Name: *Rubus idaeus*
Varietal Denomination: Sugana

(75) Inventor: Markus Kobelt, Buchs (CH)

(73) Assignee: Lubera AG, Buchs (CH)

( * ) Notice: Subject to any disclaimer, the term of this patent is extended or adjusted under 35 U.S.C. 154(b) by 0 days.

(21) Appl. No.: 12/386,799

(22) Filed: Apr. 23, 2009

(65) Prior Publication Data

US 2009/0282590 P1 Nov. 12, 2009

Related U.S. Application Data

(60) Provisional application No. 61/126,732, filed on May 8, 2008.

(51) Int. Cl.
*A01H 5/00* (2006.01)

(52) U.S. Cl. ..... Plt./204

(58) Field of Classification Search ..... Plt./204
See application file for complete search history.

*Primary Examiner*—Annette H Para
(74) *Attorney, Agent, or Firm*—The Webb Law Firm

(57) ABSTRACT

A new and distinct cultivar of *Rubus* plant named 'Sugana' having bright colored and large fruits with a long shelf life.

16 Drawing Sheets

Botanical classification: *Rubus idaeus.*
Varietal denomination: 'Sugana'.

BACKGROUND OF THE INVENTION

The present invention comprises a new and distinct cultivar of *Rubus idaeus* known by the varietal name 'Sugana'.

The new cultivar was discovered in October of 1999 in Buchs, Switzerland as part of a planned breeding program. The purpose of the breeding program was to develop better primocane raspberries with big fruits and a good shelf life. The new variety is the result of a cross between raspberry variety 'Autumn Bliss' (female parent, U.S. Plant Pat. No. 6,597) and raspberry variety 'Tulameen' (male parent, unpatented). The new variety's upright habit and high level of apical dominancy are traits that are similar to 'Autumn Bliss'. However, the new variety has brighter colored fruits and a better rooting habit than its female parent. The new variety exhibits a similar fruit size and rooting habit to 'Tulameen'. The new variety was first asexually reproduced by placing roots of motherplants in bags, cutting upcoming shoots, and rooting the cuttings under mist in Buchs, Switzerland in April of 2000. Continued observations of asexual reproductions of the new variety have confirmed that the distinguishing features of this new cultivar come true, remain stable, and are retained through successive propagations.

The following traits are determined to be basic characteristics of this new cultivar which distinguish this raspberry plant as new and distinct when compared to other varieties known to the breeder:

1. Large fruit;
2. Big drupelets;
3. Very bright, colored fruits that maintain their color well;
4. Excellent shelf life, the fruit of 'Sugana' can be marketed up to ten days after harvest;
5. Extremely high multiplication rate for a primocane variety (up to 280 young plants from one motherplant); and
6. Very high level of apical dominancy, making only 3-4 lateral shoots.

The following characteristics also distinguish 'Sugana' from other raspberry varieties known to the breeder. The characteristics are described with comparative reference to raspberry varieties 'Erika' (unpatented), 'Polka' (unpatented), and 'Himbotop' (unpatented).

1. 'Sugana' is much more upright than 'Erika' with a higher level of apical dominancy;
2. The shoots of 'Sugana' are more stable than the shoots of 'Erika';
3. 'Sugana' exhibits fewer and smaller laterals than 'Erika'. 'Sugana' exhibits 3-4 laterals while 'Erika' exhibits 6-8 laterals;
4. The branches of 'Sugana' have less anthocyanins than 'Erika' and, therefore, they are not as red as the branches of 'Erika' (see FIGS. 7 and 8);
5. In Autumn, 'Sugana' produces more new shoots from the ground than 'Erika' (see FIG. 3);
6. After propagating both varieties with roots and comparing the upcoming shoots, the propagation rate of 'Sugana' is about 20% higher than 'Erika';
7. Especially in northern climates, 'Sugana' has about 10% fewer blooms than 'Erika';
8. The fruits of 'Sugana' are about 10 to 15% bigger than the fruits of 'Erika' (see FIG. 5);
9. The color of 'Sugana' fruit is brighter than the fruit color of 'Erika' (see FIG. 5), 'Polka', and 'Himbotop';
10. 'Sugana' fruit has bigger drupelets than 'Erika';
11. 'Erika' has a higher number of, and more aggressive, thorns than 'Sugana'; and
12. 'Sugana' has fewer lateral shoots than 'Polka', 'Erika', and 'Himbotop'.

DESCRIPTION OF THE DRAWINGS

The accompanying photographic drawings illustrate the new cultivar and comparison varieties, with the colors being as nearly true as possible with color illustrations of this type.

DESCRIPTION OF THE NEW PLANT

'Sugana' has not been observed under all possible environmental conditions. The phenotype may vary somewhat with variations in environment, such as temperature, day length, and light intensity. However, there is no variance in genotype.

In the following description, color references are made to The Royal Horticultural Society Colour Chart, except where general terms of ordinary dictionary significance are used. Plants of the new variety were planted in a 10 liter pot at the end of March in Buchs, Switzerland, and the descriptions herein were observed in the middle of October of the same year, so the plants were approximately 7 months old when described. The plants were grown in their containers under field conditions. The measurements were taken under natural light in a greenhouse.

PLANT

Primary use: 'Sugana' is primarily grown for its primocane fruit.

Time to initiate roots: 14 days at 18-19° C., under mist.

Time to produce a rooted plant: 40-45 days, including acclimatization/hardening time.

Rooting habit: Very good; young plants typically produce 3-5 roots that branch and fill a 5 cm. container.

Form: Very upright plant with 3-4 fruiting laterals.

Height (from soil to top of plant): 170-200 cm.

Plant diameter: 70-80 cm.

Vigor: Medium to high.

Disease/pest resistance: Medium tolerance to *Phytophthora,* especially when planted in the field. When planted with a row of 'Polka' which died from *Phytophthora,* the 'Sugana' plant is still growing and fruiting for 2 years now. On the other hand, some *Phytophthora* losses have occurred when 'Sugana' was cultivated in pots.

Weather tolerance: Tolerance to rain is better than 'Autumn Bliss', but not very good. In windy locations there can be some fruit damage because of the spines/thorns of 'Sugana'.

Primocane:

*Average number of canes per plant.*—A one-year old culture has 1-2 canes per plant. Later on, there are at least 3-5 canes. Late in the season, especially, 'Sugana' produces many new shoots from the ground.

*Average length.*—170-200 cm. (1 year old culture).

*Average diameter.*—0.8-1.0 cm.

Figure 9:
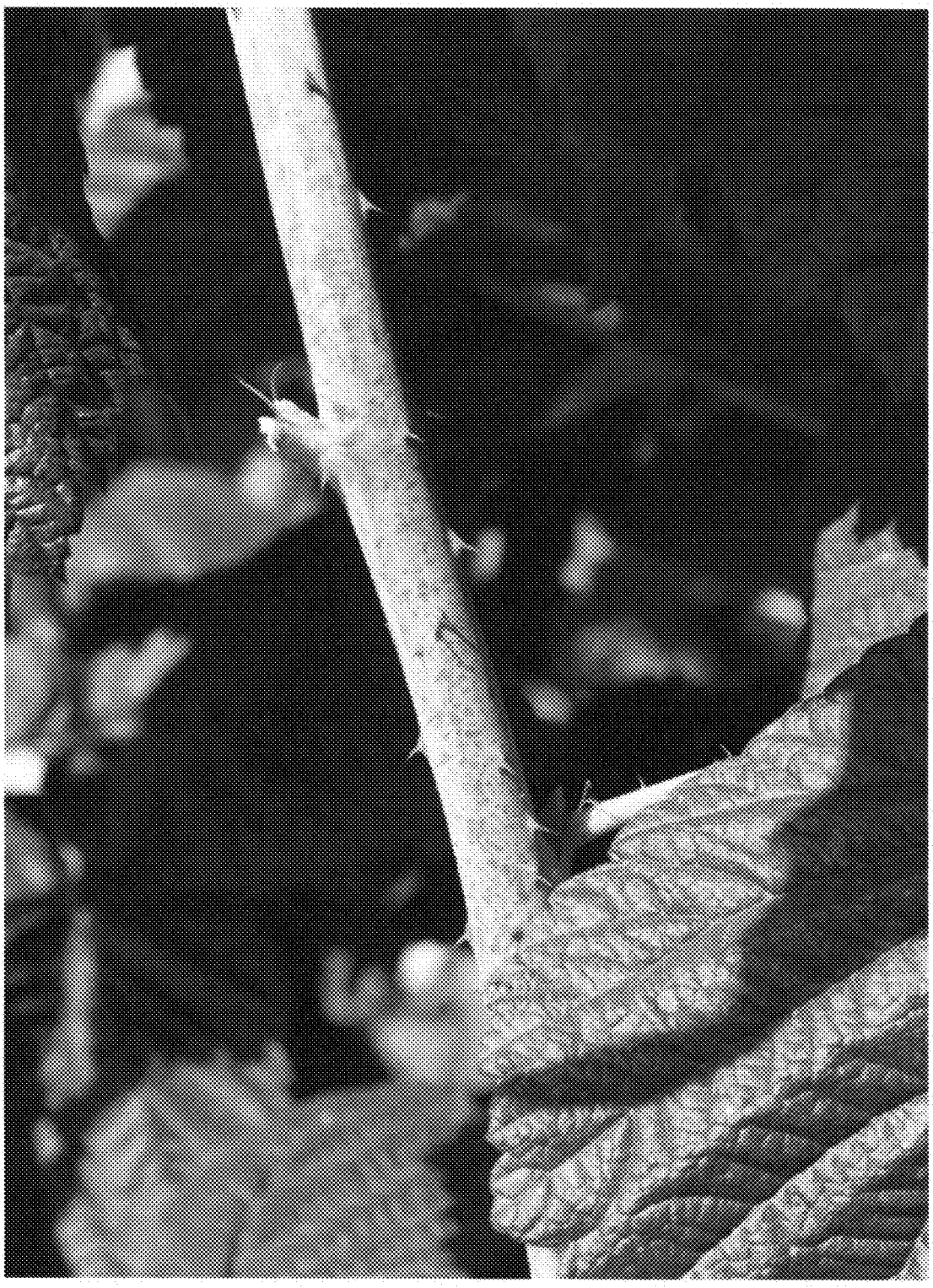
FIG. 9 illustrates the color of 'Sugana' shoots.
Figure 10:
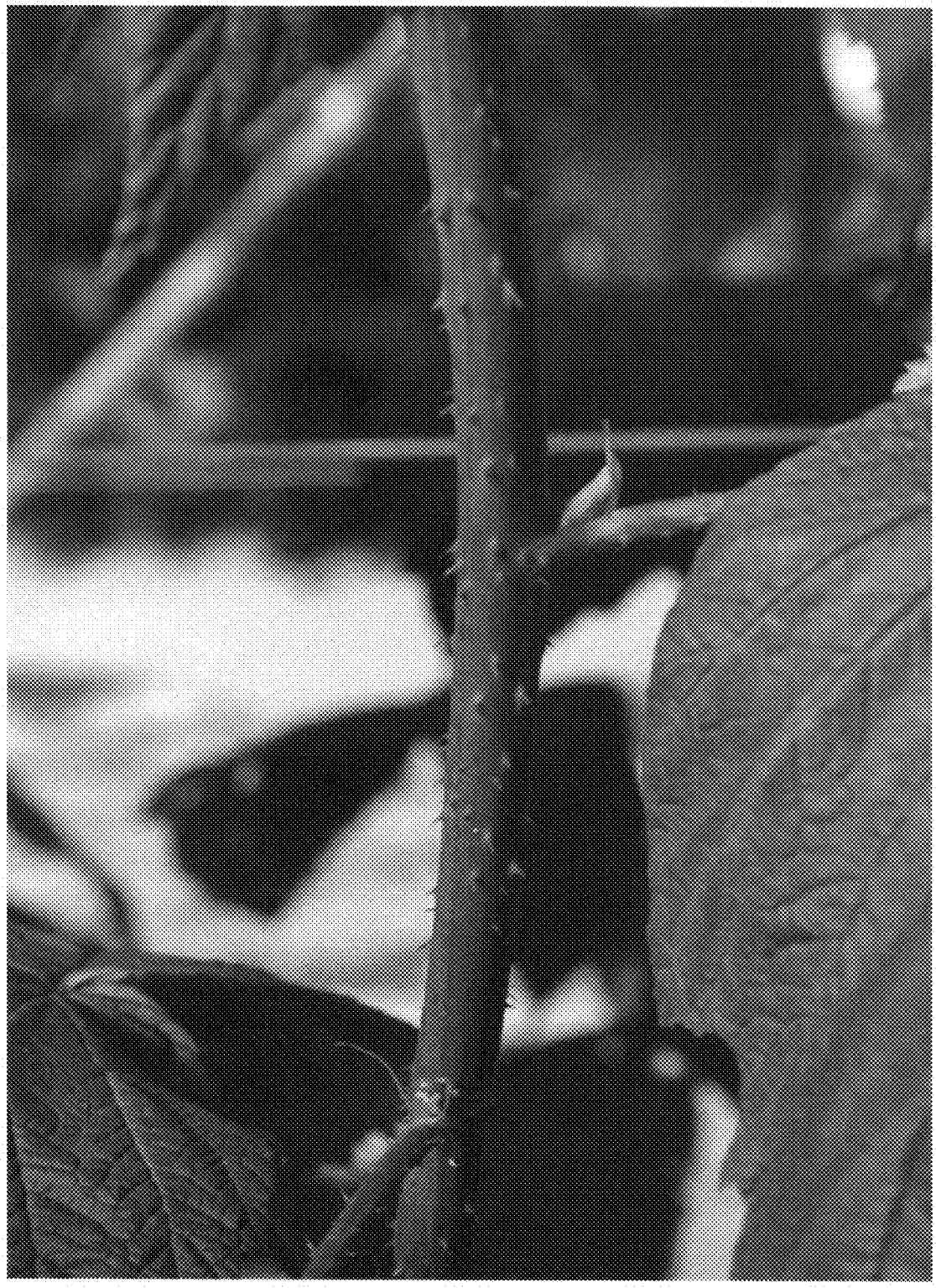
FIG. 10 illustrates the color of 'Polka' shoots.

*Fruiting cane color.*—142C, with some red coloration on the sunny side of the canes (see FIG. 9), but less red than 'Polka' (see FIG. 10) and 'Erika' and about the same as 'Autumn Bliss'.

*Dormant cane color.*—Brownish-grey.

*Number of fruiting laterals per cane.*—3-4.

*Internode length.*—5.3 cm.

*Young shoot color.*—142C.

Figure 11:
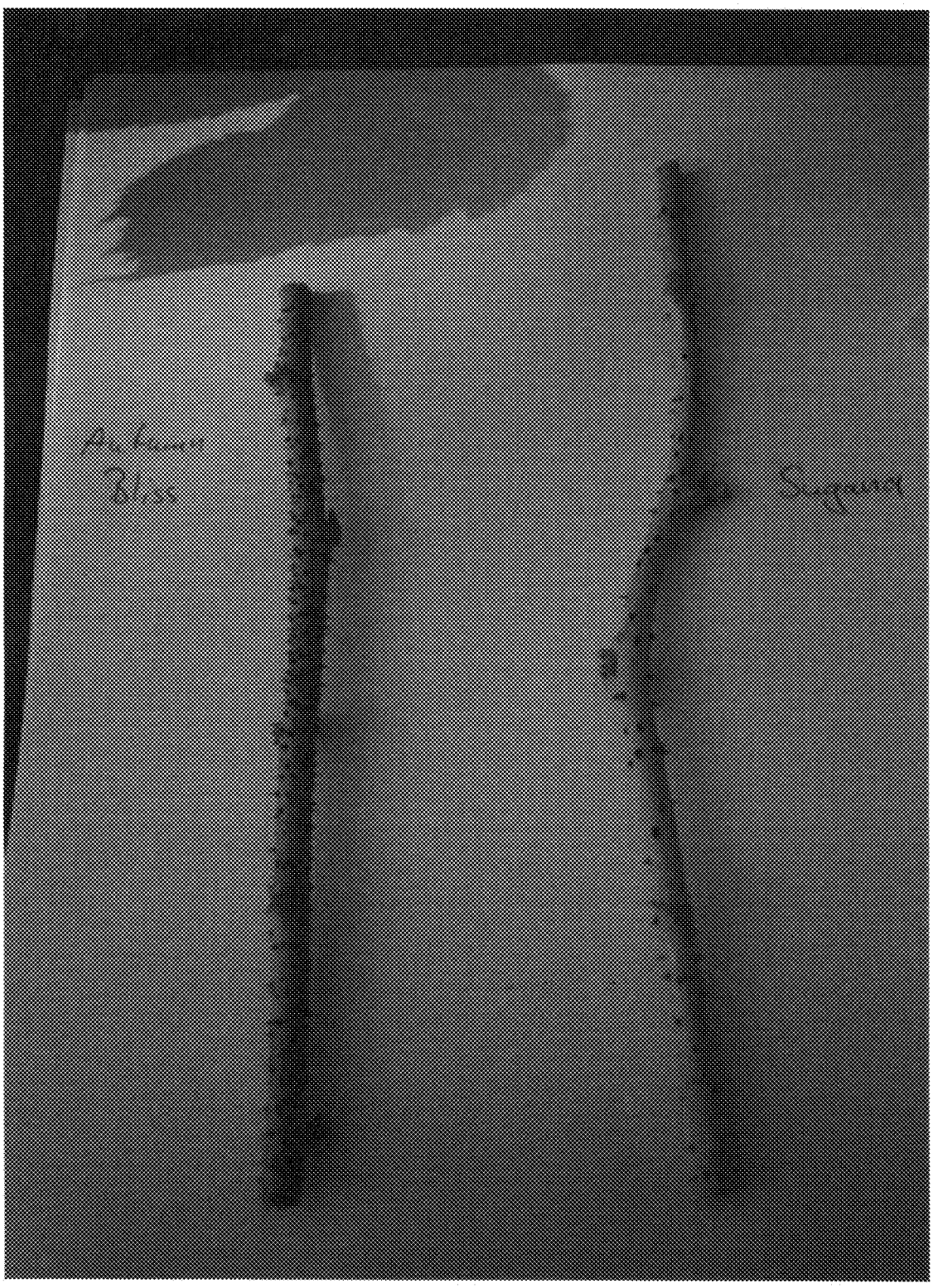
FIG. 11 is a photograph of the thorns of 'Sugana' and 'Autumn Bliss'.

Thorn:

*Density.*—Medium, less than 'Autumn Bliss' (see FIG. 11) and 'Erika'.

*Length.*—2-2.5 mm.

*Color.*—Dark red to violet.

*Texture.*—Relatively hard, but the tips soon break.

Figure 12:
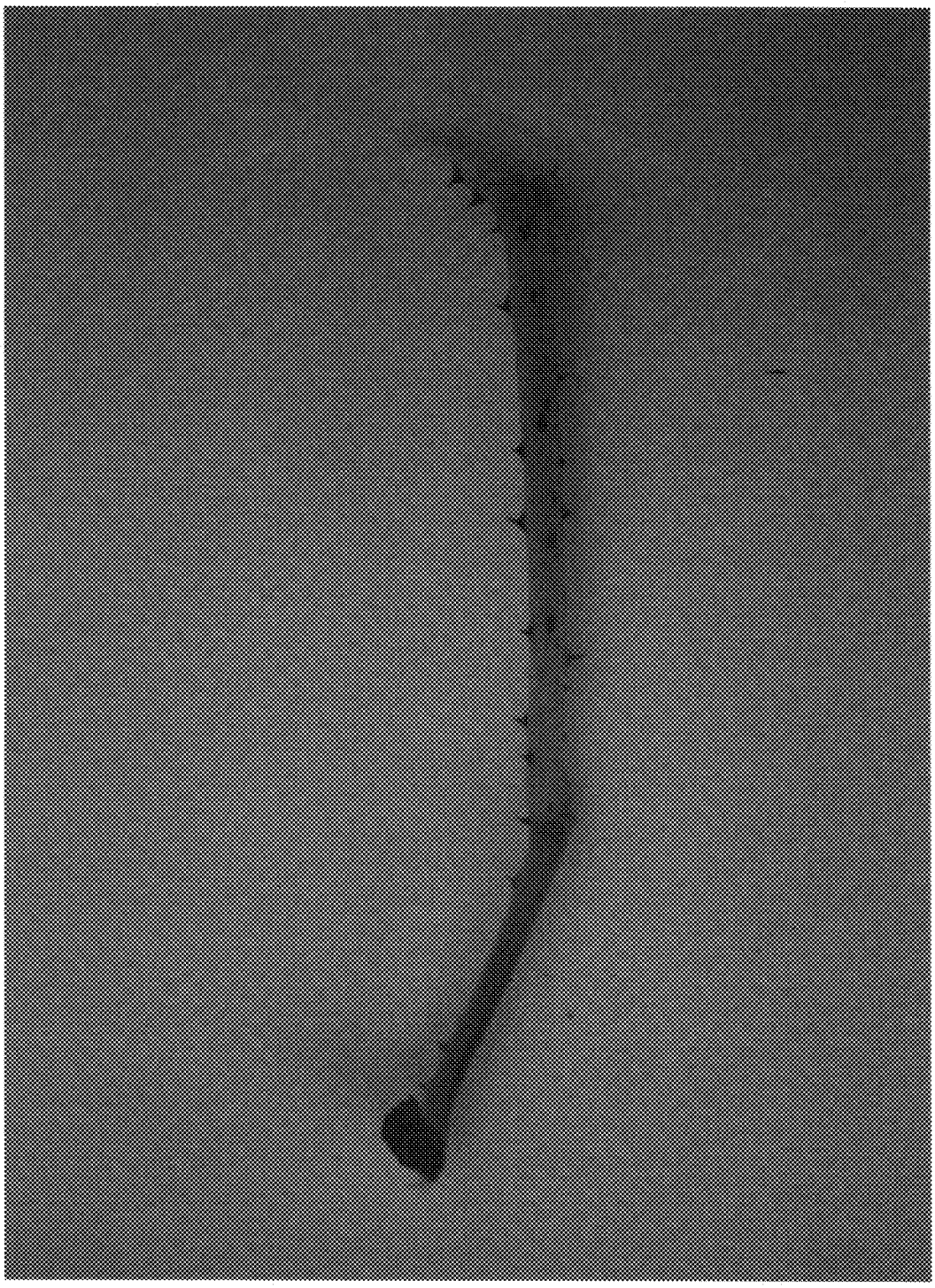
FIG. 12 is a photograph of the thorns of 'Sugana'.

*Tip attitude.*—Pointing slightly backwards (see FIG. 12).

Foliage:

*Arrangement.*—Compound.

*Number of leaves per stem.*—Usually 3, sometimes 5.

*Fragrance.*—None present.

Petiole:

*Length.*—7-8 cm.

*Diameter.*—2.5 mm.

*Color.*—Pale green.

*Texture.*—Very thin hairs present.

Figure 13:
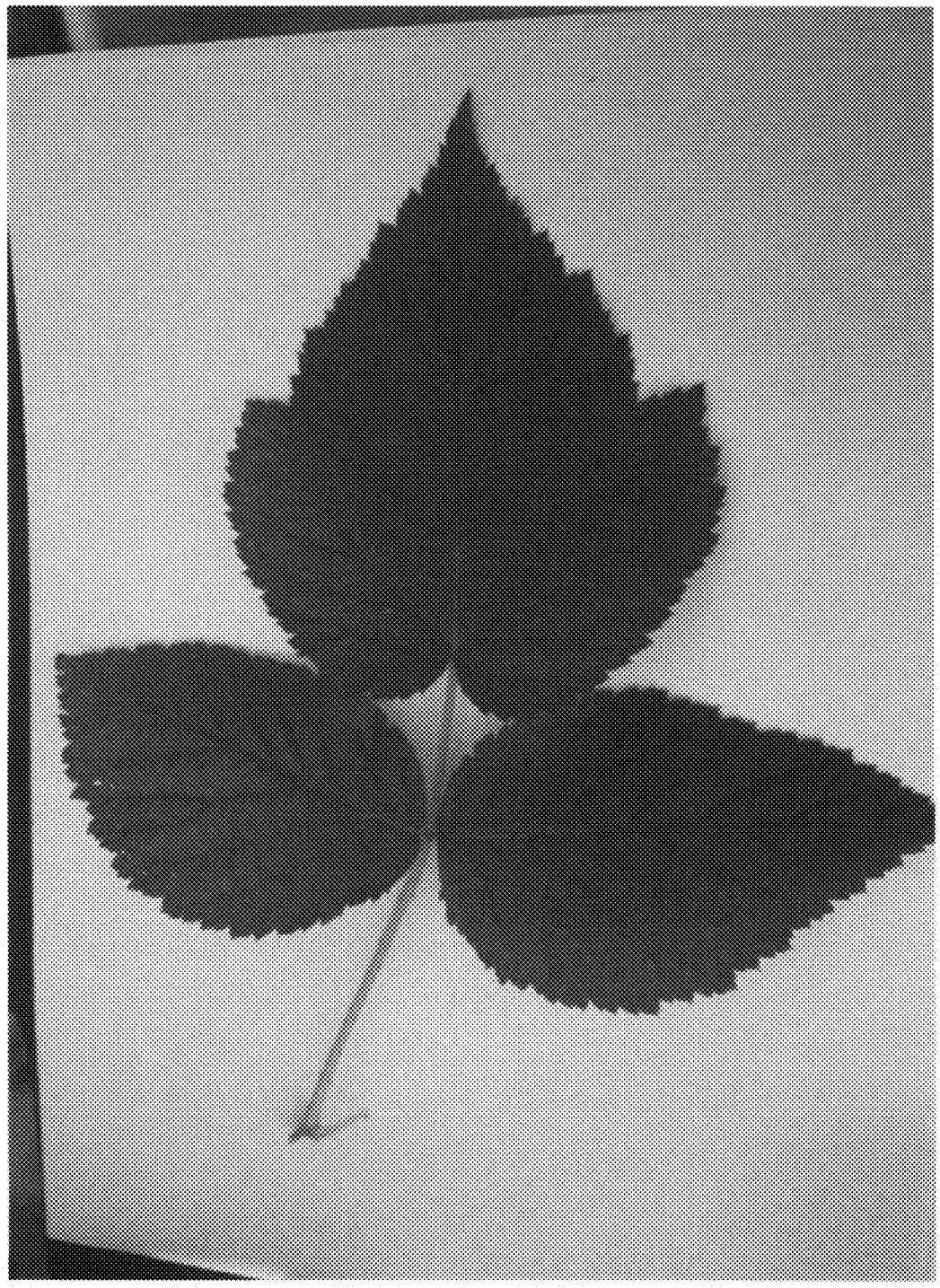
FIG. 13 illustrates the upper surface of young leaflets of 'Sugana'.

Young leaflet color:

*Upper surface.*—142A (see FIG. 13).

Figure 14:
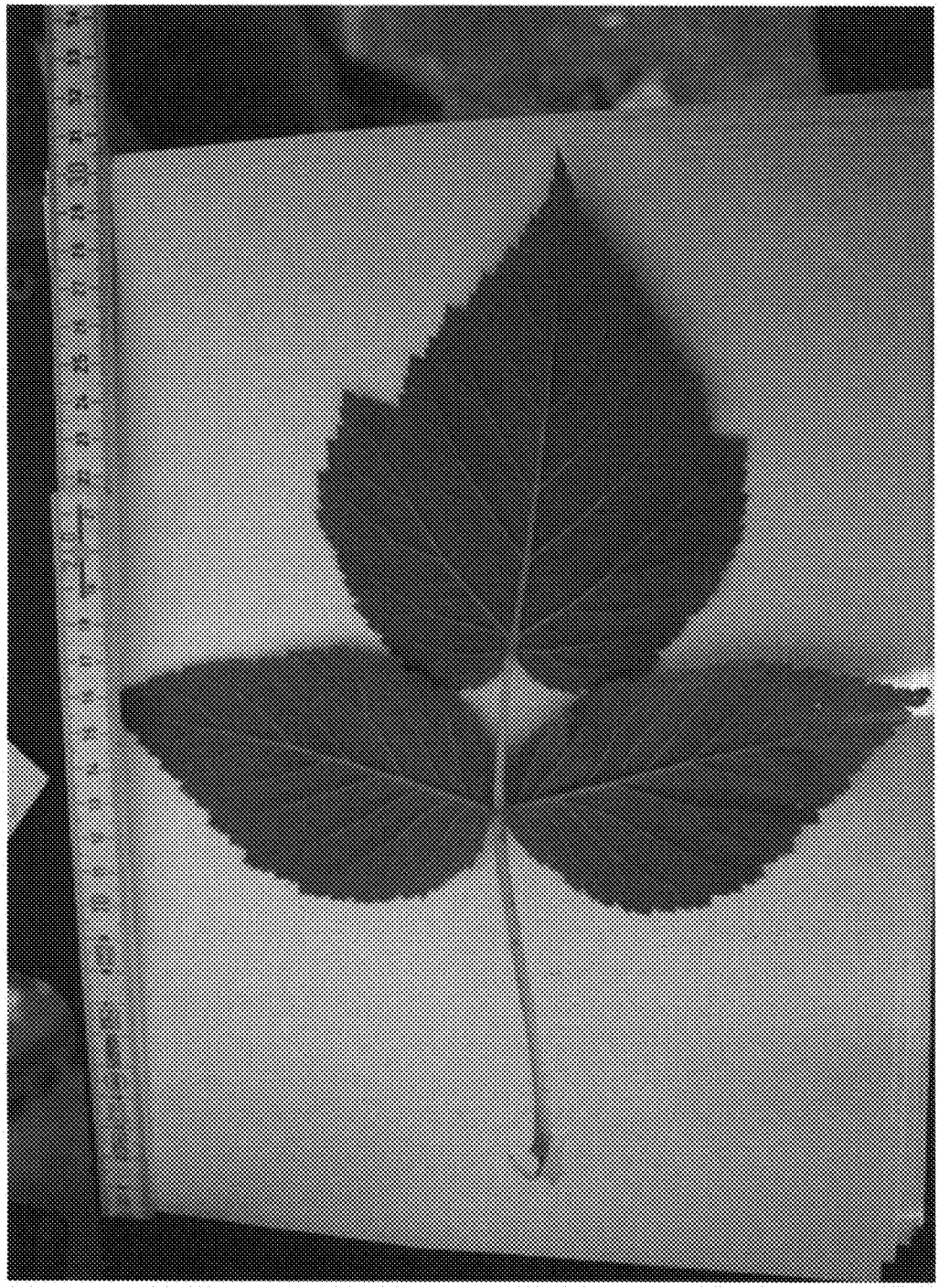
FIG. 14 illustrates the lower surface of young leaflets of 'Sugana'.

*Lower surface.*—143B and the veins are green. Between the veins there are thin grew hairs which provide a greyish impression (see FIG. 14).

Figure 15:
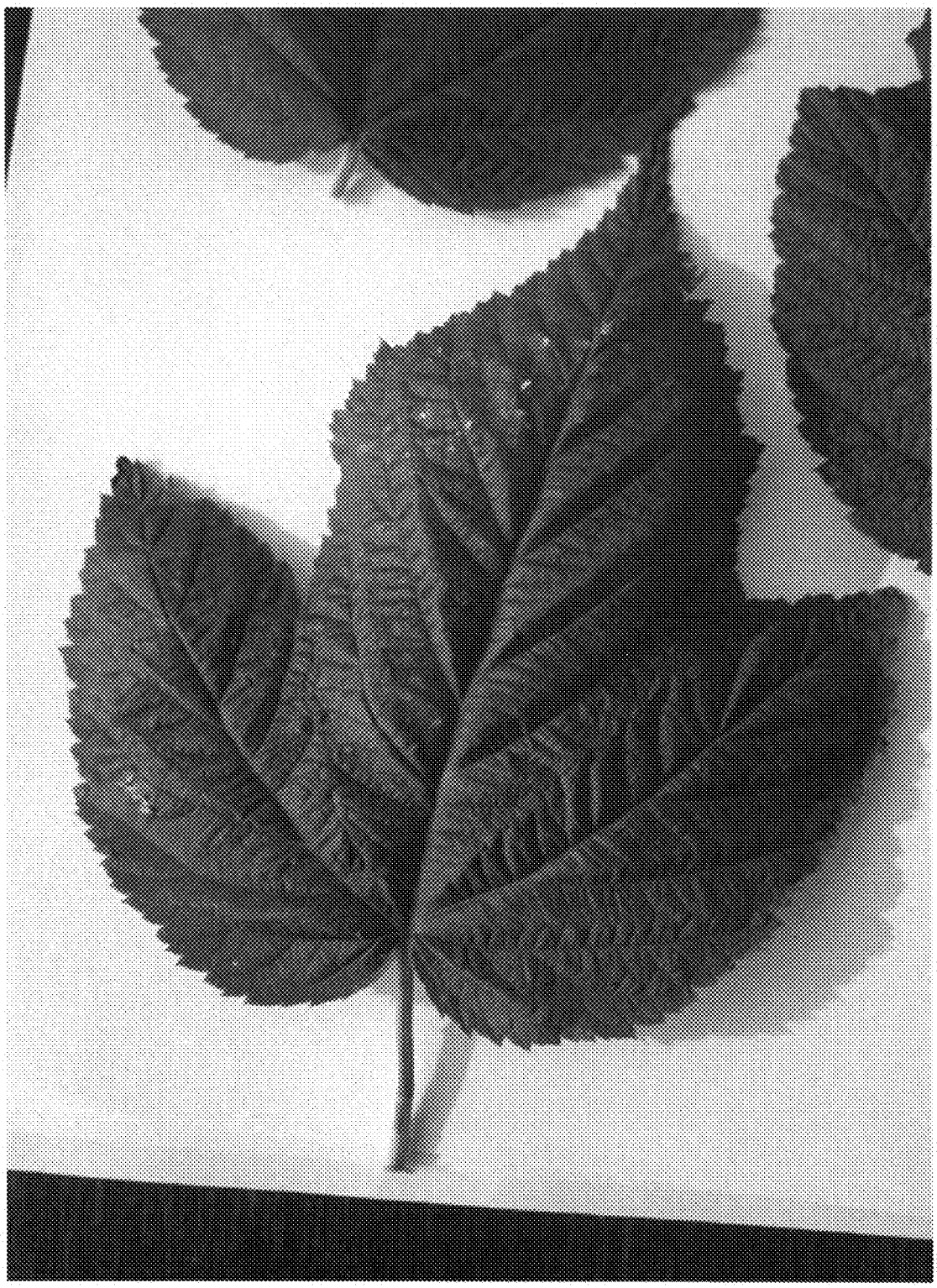
FIG. 15 illustrates the upper surface of mature leaflets of 'Sugana'.

Mature leaflet color:

*Upper surface.*—142A (see FIG. 15).

Figure 16:
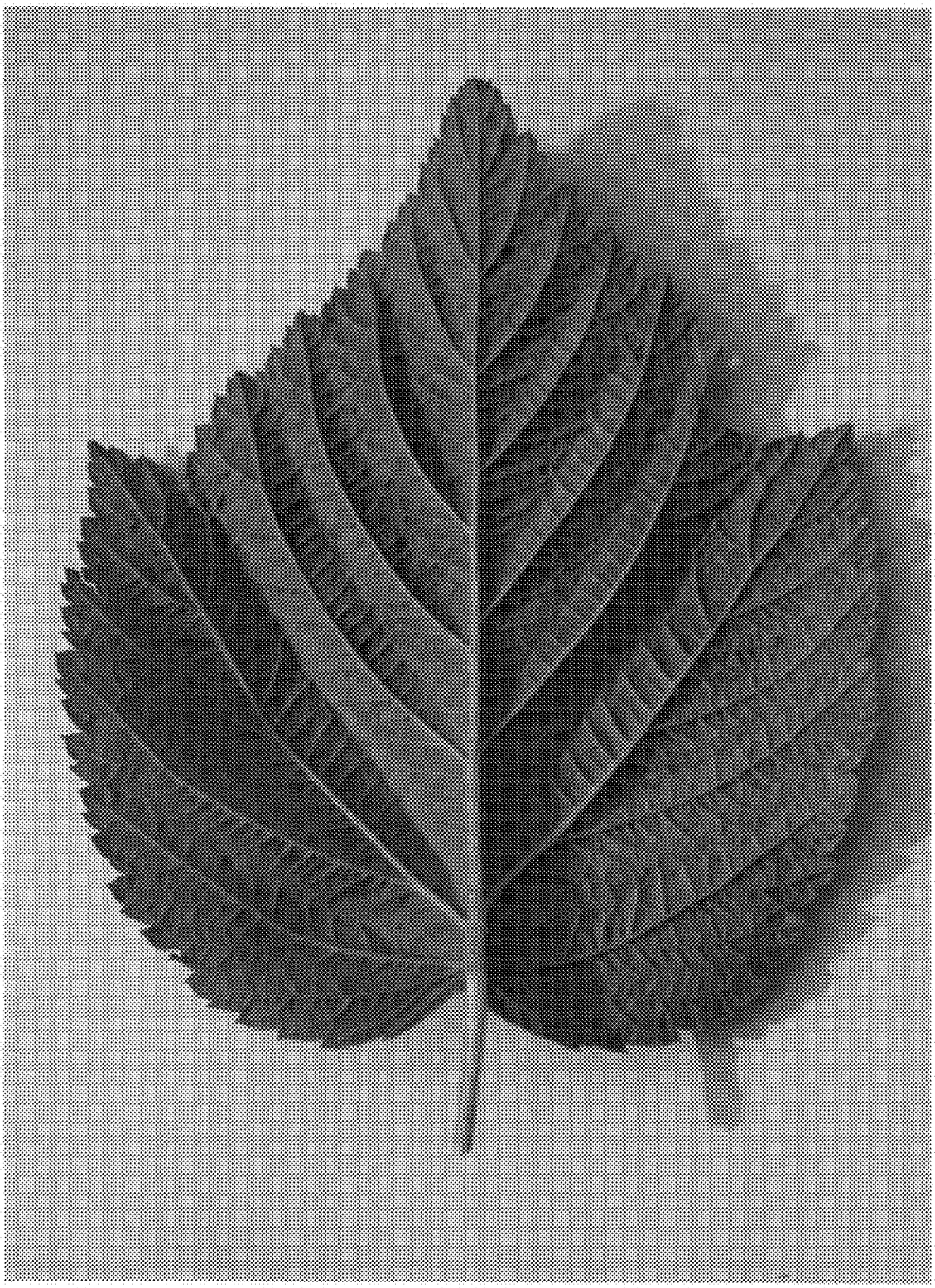
FIG. 16 illustrates the lower surface of mature leaflets of 'Sugana'.

*Lower surface.*—143B and the veins are green. Between the veins there are thin grew hairs which provide an overall grey impression (see FIG. 16).

Lateral leaflets:

*Length.*—9.5-10.5 cm.

*Width.*—5.5-6.8 cm.

*Shape of leaf* (*generally*).—Ovate.

*Shape of apex.*—Cuspidate.

*Shape of base.*—Cordate.

*Texture.*—Soft.

*Margin type.*—Doubly serrate.

Terminal leaflets:

*Length.*—13.5-14.5 cm.

*Width.*—9-12.5.

*Shape of leaf* (*generally*).—Rather irregular; ovate.

*Shape of apex.*—Cuspidate.

*Shape of base.*—Cordate.

*Texture.*—Harder and firmer than lateral leaflets.

*Margin type.*—Doubly serrate.

Veins:

*Upper surface color.*—145C.

*Lower surface description.*—145C in color, with some small thorns present.

Figure 1:
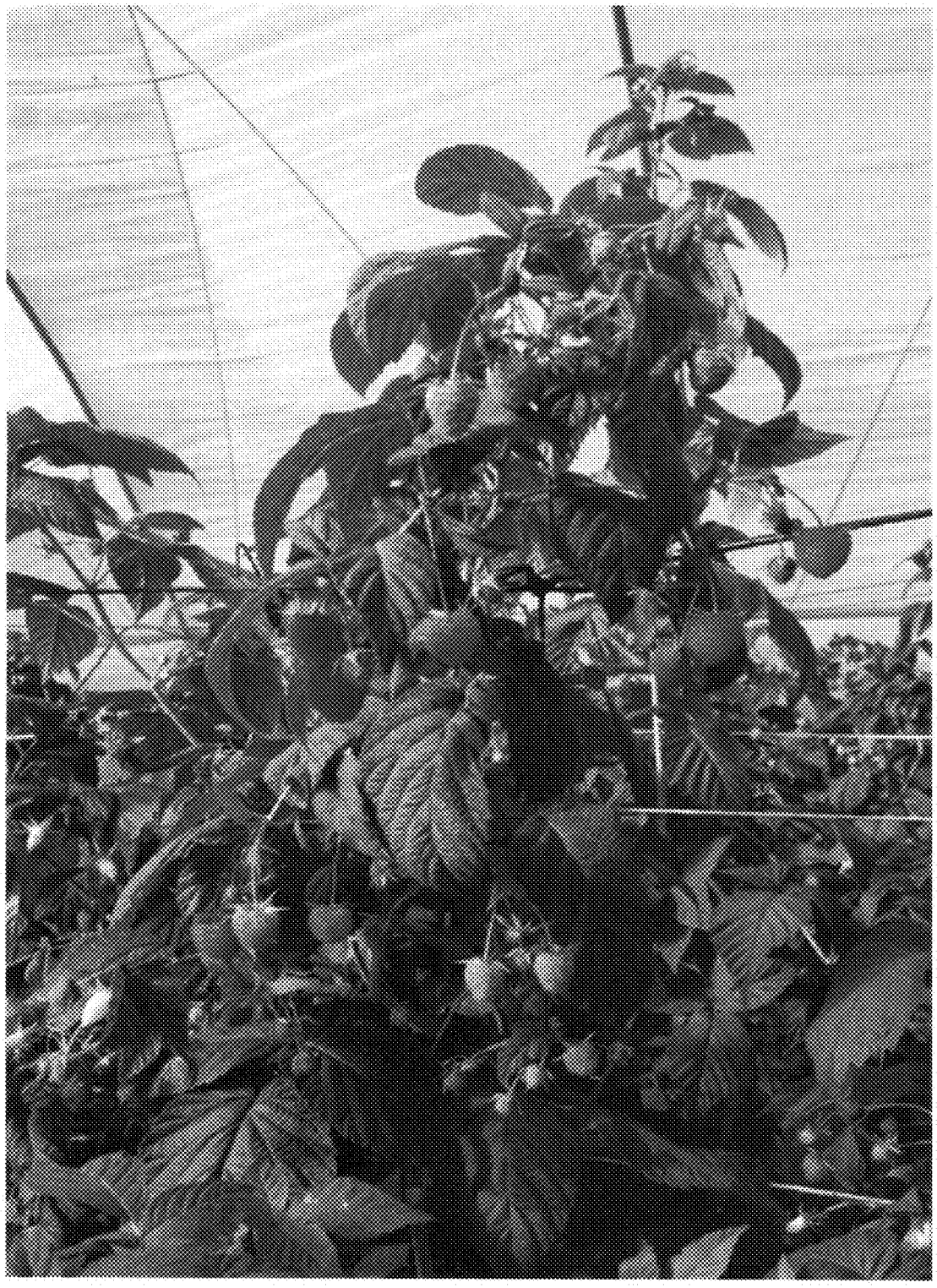
FIG. 1 is a photograph of an entire plant of the new variety.
Figure 2:
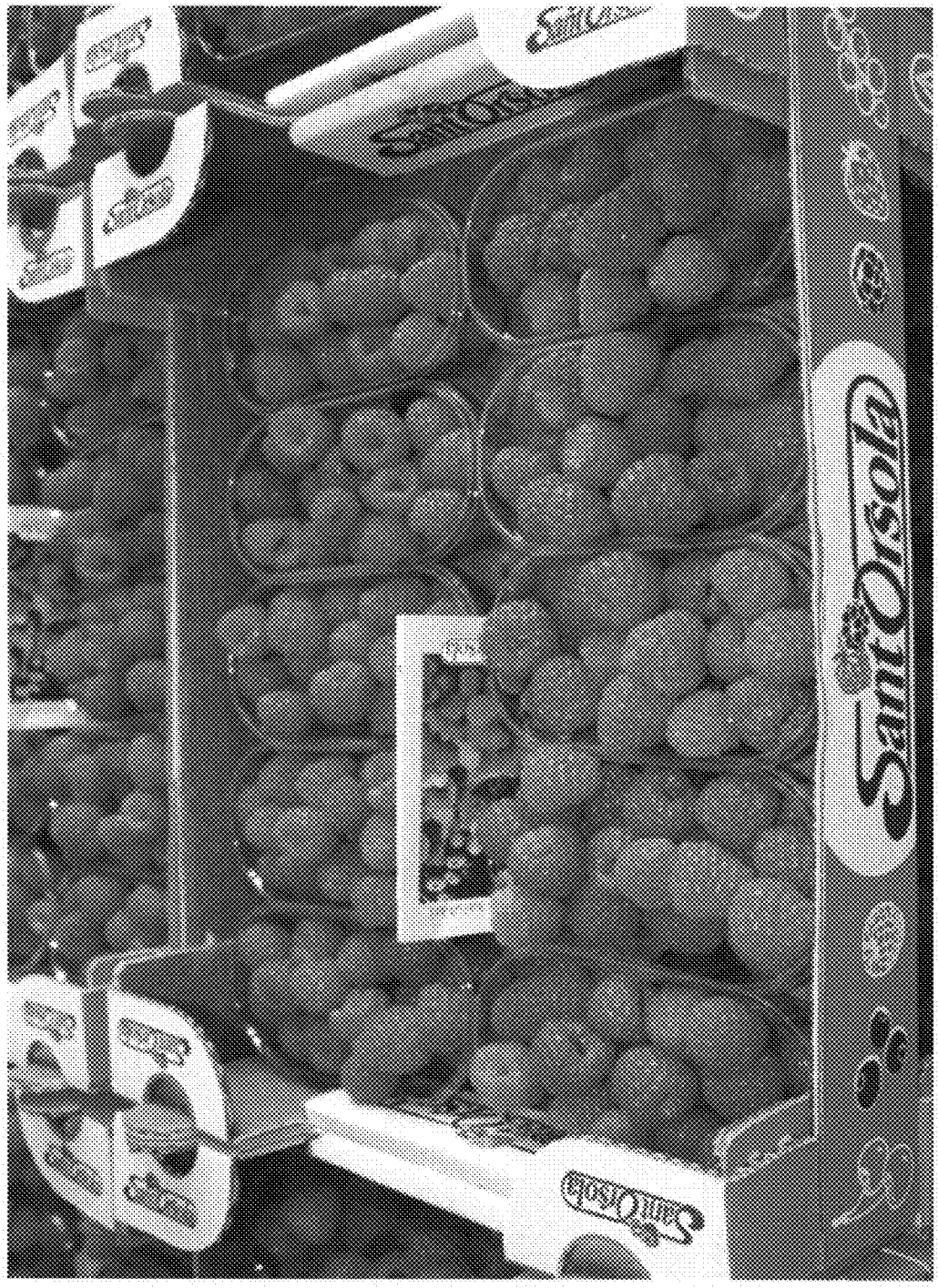
FIG. 2 is a photograph of 'Sugana' fruit one day after harvest.
Figure 3:
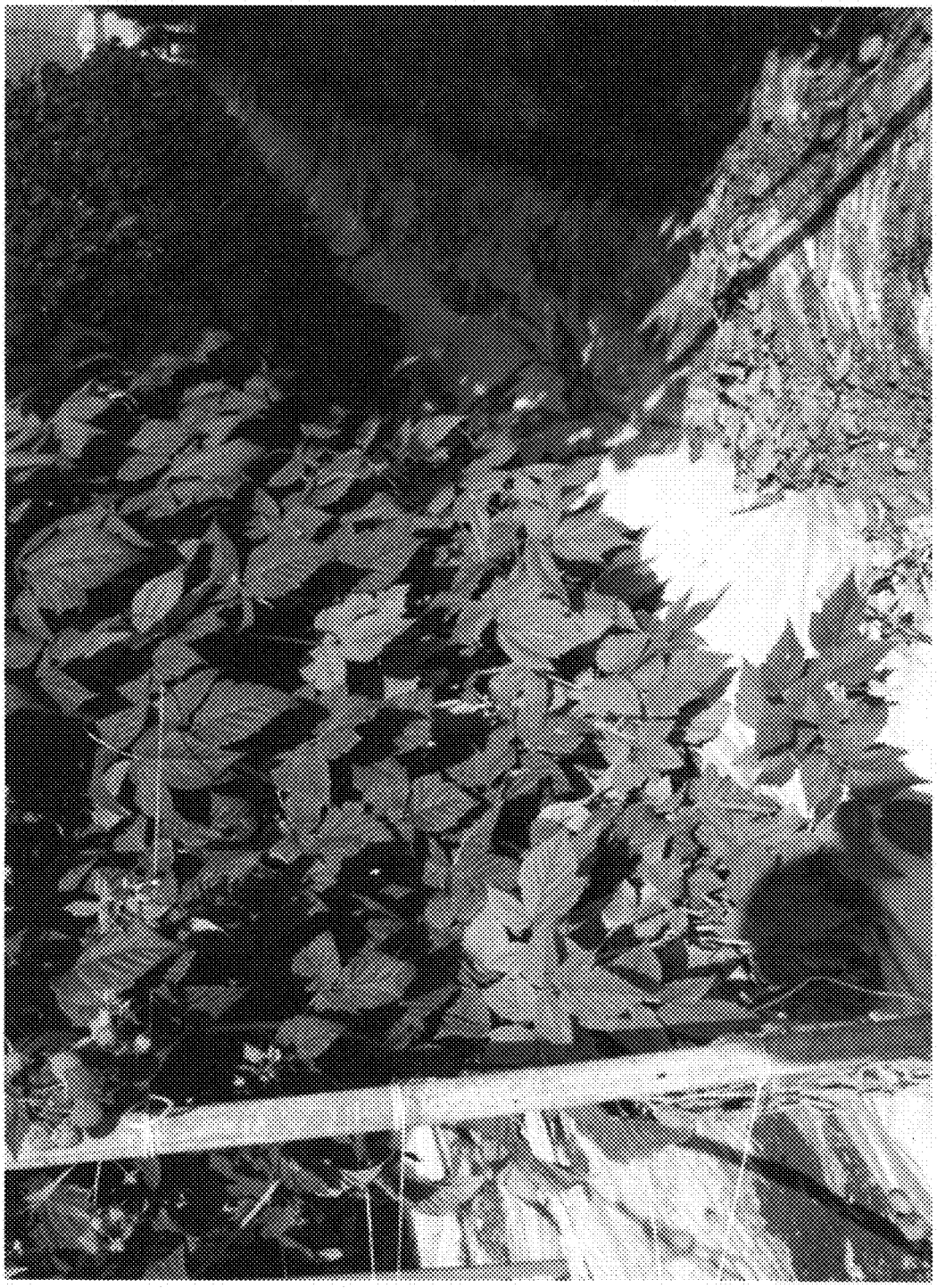
FIG. 3 illustrates the new shoots of 'Sugana' in October.
Figure 6:
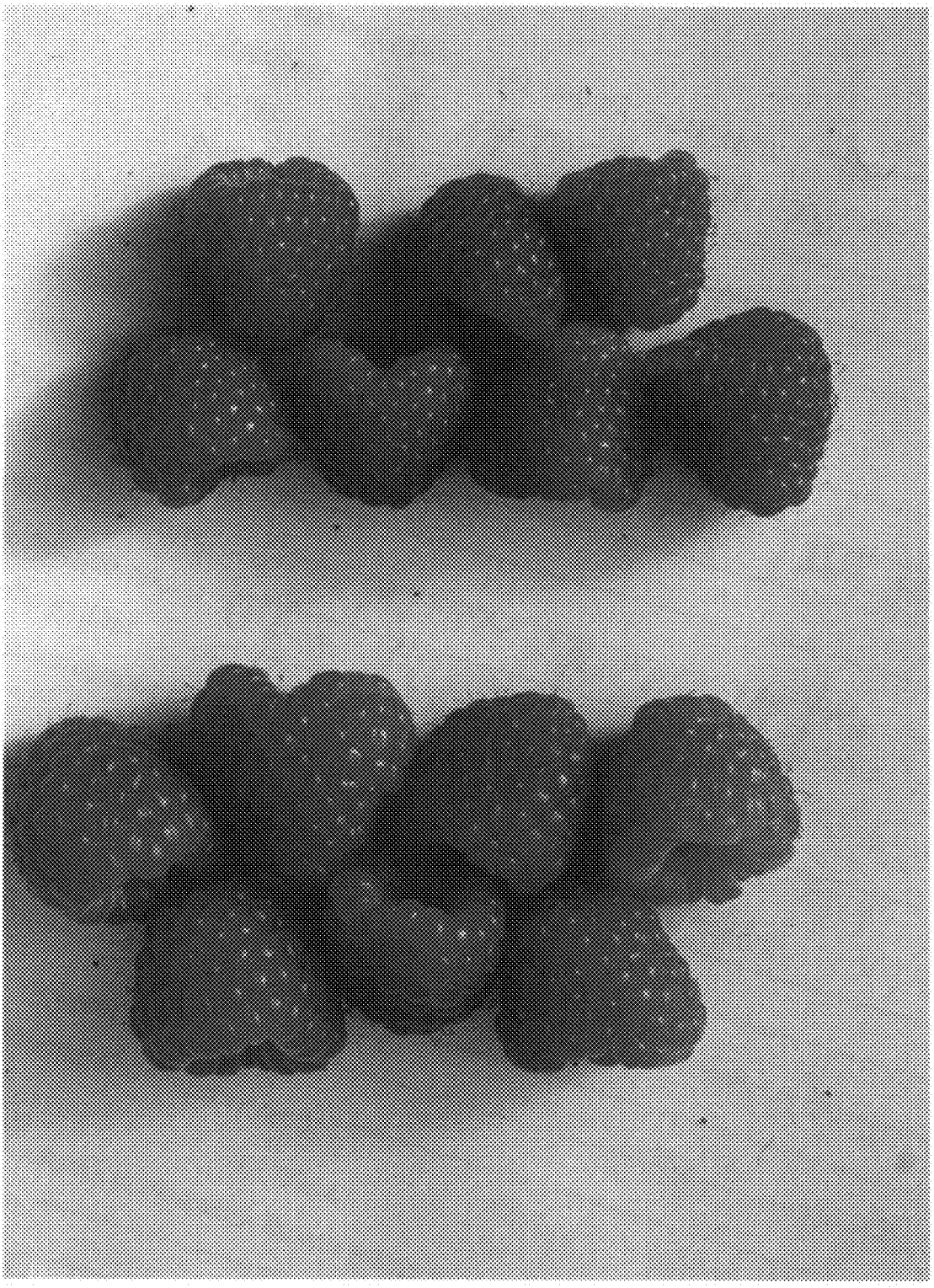
FIG. 6 illustrates the fruits of 'Sugana' (top) in comparison with the fruits of 'Polka' (bottom)
Figure 7:
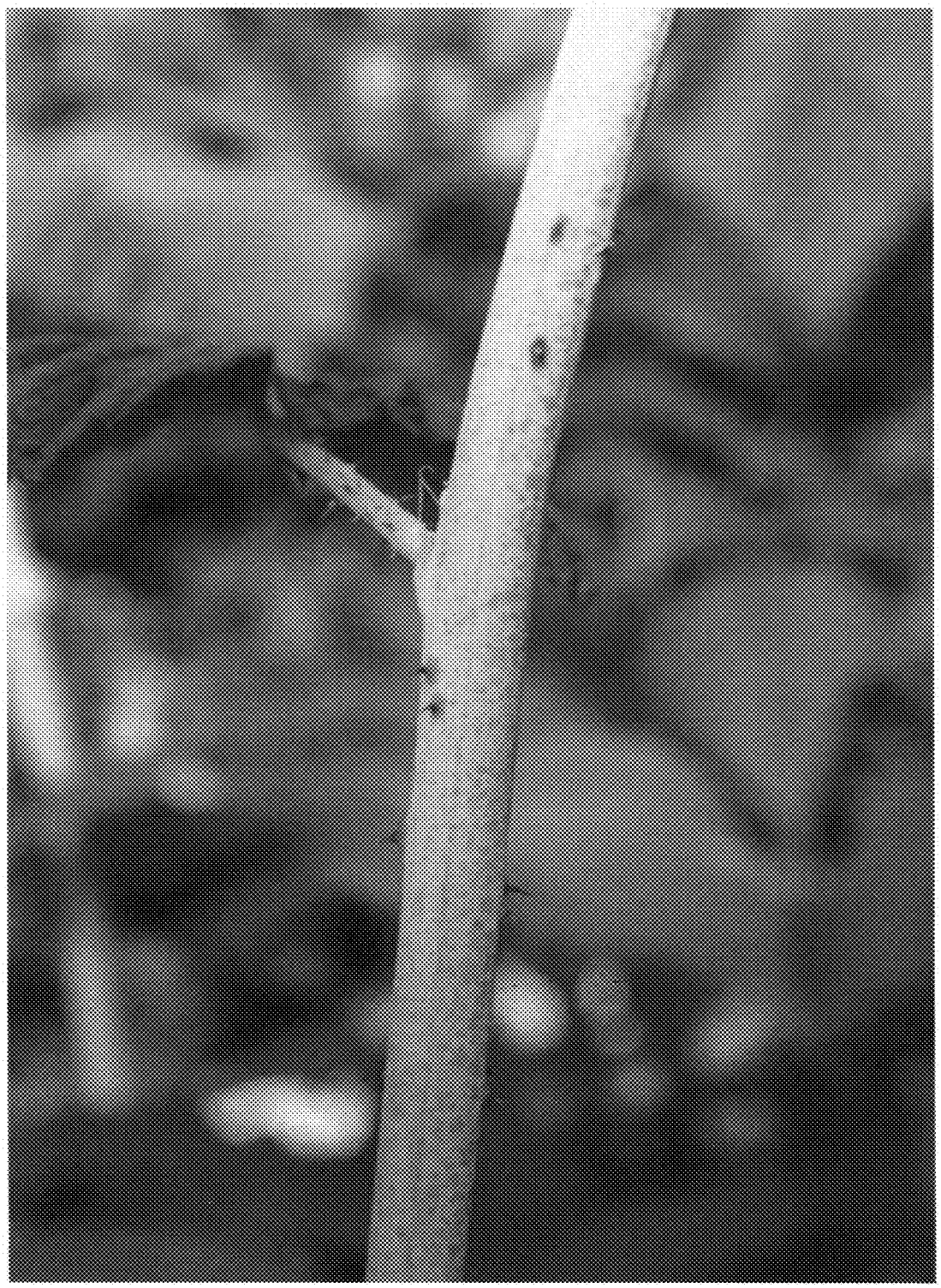
FIG. 7 illustrates the thorns and color of 'Sugana' canes.
Figure 8:
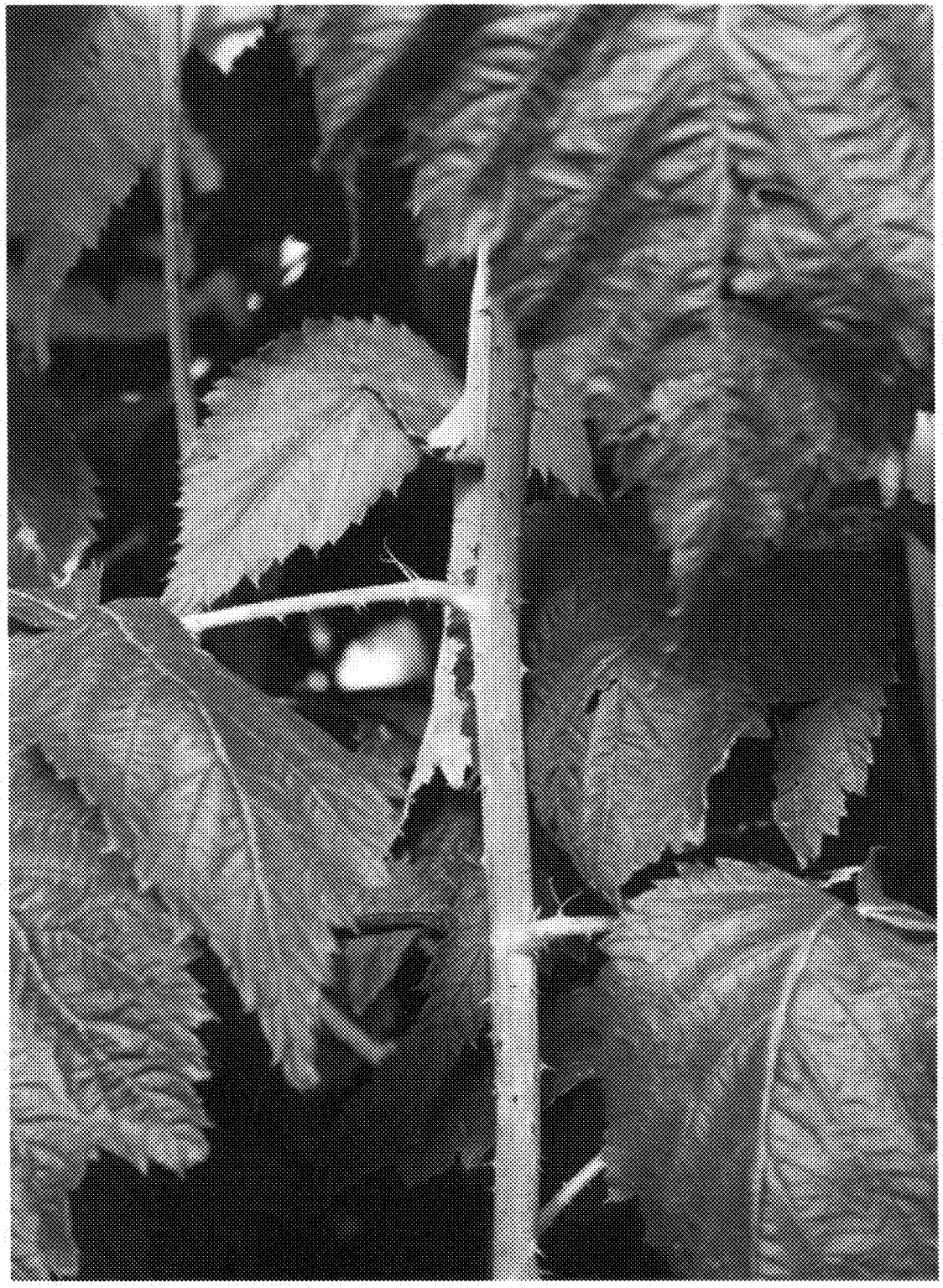
FIG. 8 illustrates the thorns and color of 'Erika' canes.

Fruit (see FIGS. 1 and 6):

*Harvest season.*—The third week of August until October on primocanes; in June on floricanes.

*Number of fruit per fruiting lateral.*—13-21.

*Immature color.*—43D.

*Maturing color.*—42B.

*Mature color.*—After storage of about 1 week, the color of 'Sugana' is rather stable and a really red color, 41B (not violet like other varieties).

*Taste.*—Agreeable; the same level of sweetness as 'Polka', but with more acidity.

*Length.*—2.8-2.9 cm.; in the mountains, such as the province Trento of Italy, the fruit can be more than 3 cm. in length.

*Width.*—2.6-2.7 cm.

*Overall shape.*—Round to conical. In the beginning of the season, the fruits are more conical, and afterwards they become more round. In more northern climates, the fruits are also more conical than in more southern or Mediterranean climates.

*Glossiness.*—Medium; less so than fruits of 'Erika' and 'Polka'.

*Weight.*—6 grams; in the mountains, in more northern climates, and in the beginning of the fruiting season, fruits can be 2-3 grams bigger.

*Drupelet size.*—Big to very big; sometimes more than 3 mm. and much bigger than 'Polka'.

*Drupelet number.*—100-120 drupelets per fruit.

*Drupelet arrangement.*—Rather irregular.

*Flesh firmness.*—Rather firm; less firm than 'Polka', but only because the fruitflesh-seed ratio is much better with 'Sugana'.

*Skin firmness.*—Very good; much firmer than 'Autumn Bliss' and 'Polka'. The skin of the drupelets seems to be very elastic.

*Receptacle/torus length.*—1.6-2 cm.

*Receptacle/torus width.*—1-1.2 cm.

*Adherence of berry to receptacle.*—The berries can be picked much easier than with 'Polka' and 'Erica'.

Reproductive organs:

*Pistil number per flower.*—70-90.

*Pistil size.*—Medium.

*Stamen number per flower.*—85-105.

*Stamen size.*—Medium.

Figure 4:
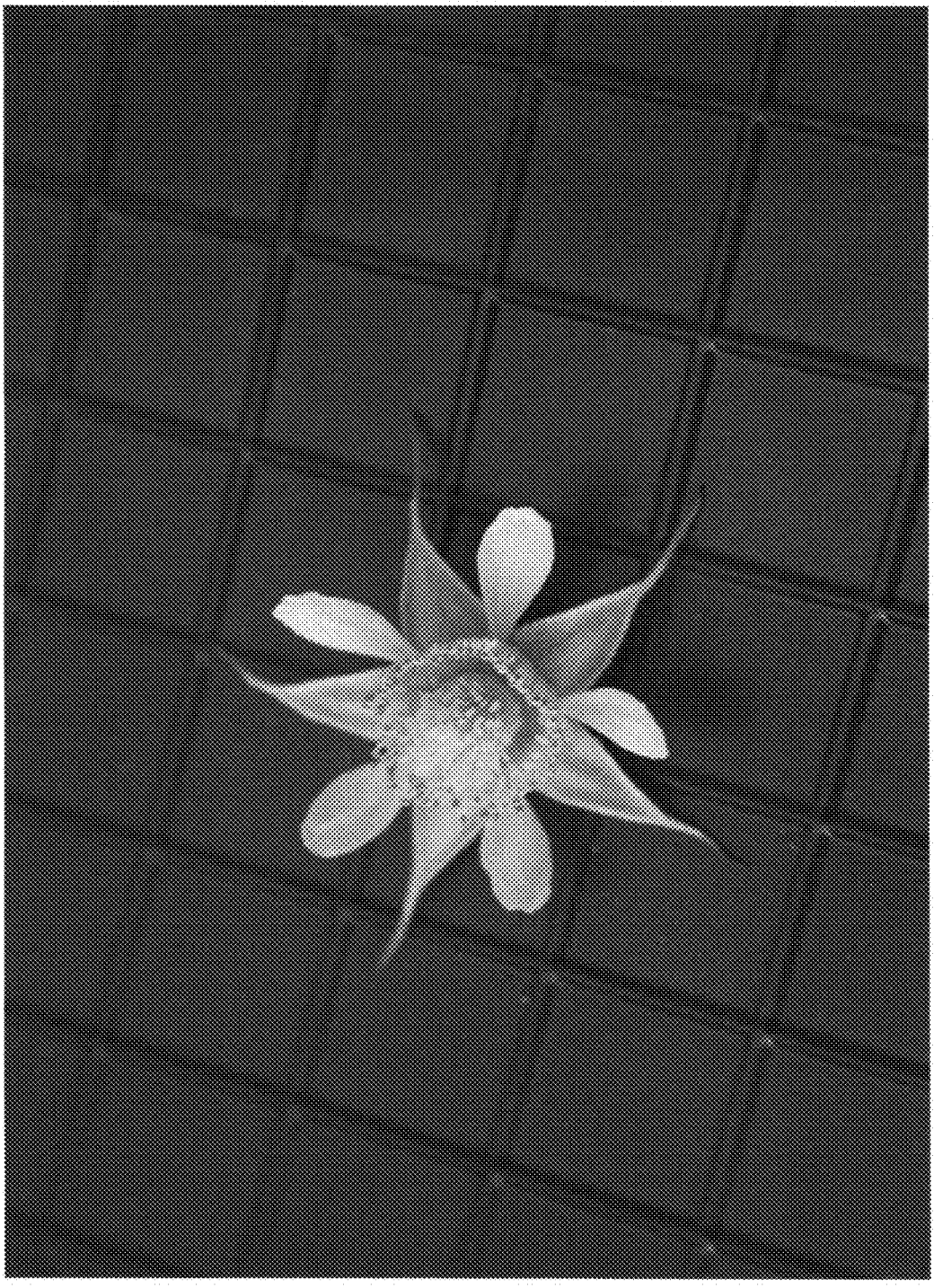
FIG. 4 is a close-up photograph of a flower of 'Sugana'.
Figure 5:
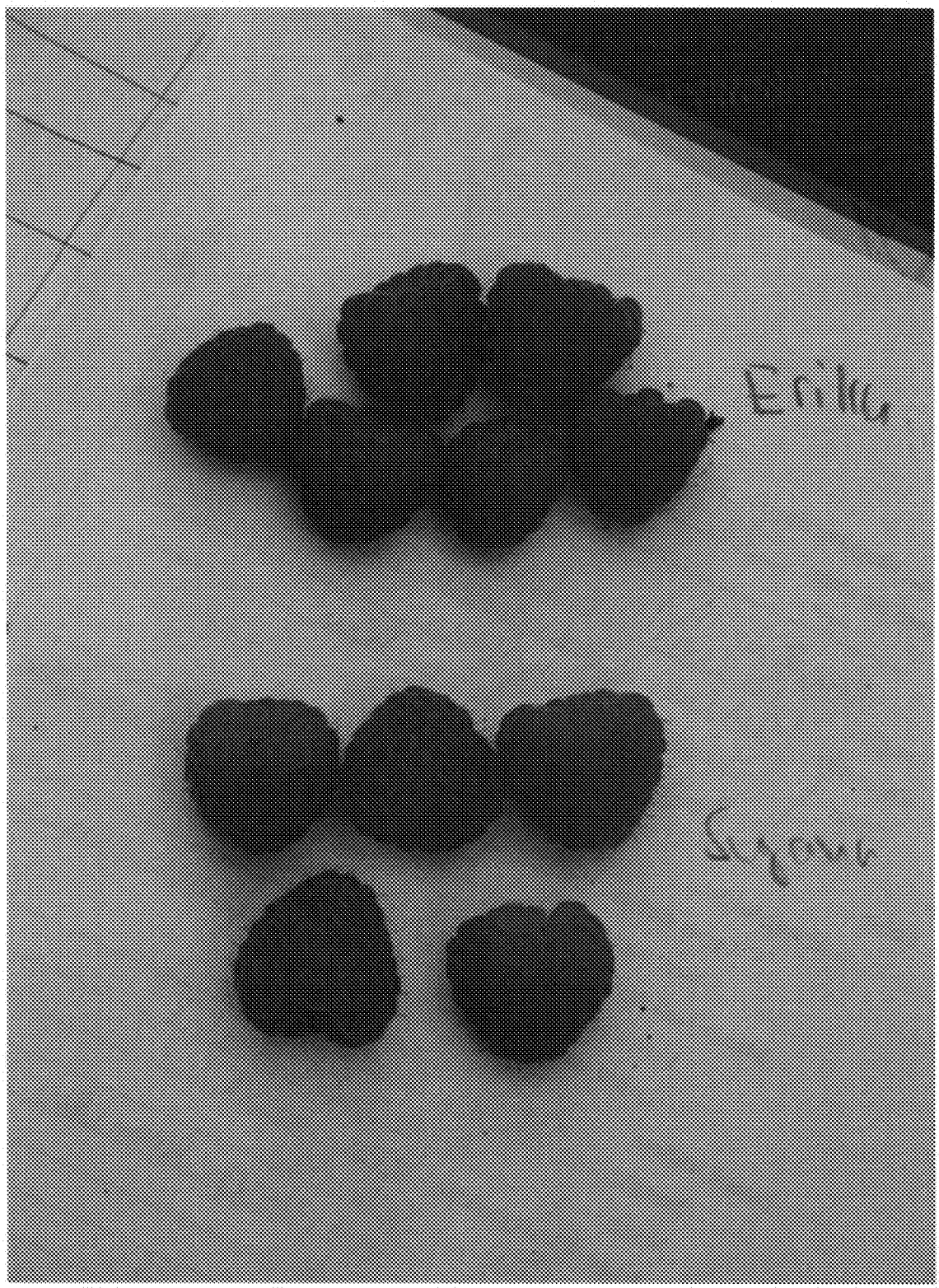
FIG. 5 illustrates the fruits of 'Sugana' in comparison with the fruits of 'Erika'.

Flowers (see FIG. 4):

*Natural flowering season.*—In Buchs, Switzerland, the primocanes of 'Sugana' flower from the end of June to August/September, and the floricanes flower from the end of April until May.

*Number of flowers per plant.*—150-200.

*Color.*—155D.

*Flower height.*—0.8 cm.

*Flower diameter.*—3.1 cm.

I claim:

1. A new and distinct variety of *Rubus* plant named 'Sugana' as herein described and illustrated.

* * * * *

UNITED STATES PATENT AND TRADEMARK OFFICE

CERTIFICATE OF CORRECTION

PATENT NO. : PP21,357 P3
APPLICATION NO. : 12/386799
DATED : October 5, 2010
INVENTOR(S) : Kobelt It is certified that error appears in the above-identified patent and that said Letters Patent is hereby corrected as shown below:

Title Page, Column 1, after the "Varietal denomination: 'Sugana" and before the "BACKGROUND OF THE INVENTION", insert the following:

--CROSS-REFERENCE TO RELATED APPLICATIONS

This application claims the benefit of U.S. Provisional Plant Patent Application No. 61/126,732 filed May 8, 2008, which is hereby incorporated by reference in its entirety. --

Signed and Sealed this
First Day of March, 2011

David J. Kappos

David J. Kappos
*Director of the United States Patent and Trademark Office*